US012797521B2

(12) United States Patent
Kuramoto

(10) Patent No.: US 12,797,521 B2
(45) **Date of Patent: *Nov. 17, 2026**

(54) ENDOSCOPIC SUBMUCOSAL INJECTION MATERIAL

(71) Applicant: FUJIFILM Corporation, Tokyo (JP)

(72) Inventor: Mamoru Kuramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 229 days.

This patent is subject to a terminal disclaimer.

(21) Appl. No.: 18/537,725

(22) Filed: Dec. 12, 2023

(65) Prior Publication Data

US 2024/0123125 A1 Apr. 18, 2024

Related U.S. Application Data

(63) Continuation of application No. PCT/JP2022/018075, filed on Apr. 18, 2022.

(30) Foreign Application Priority Data

Jun. 16, 2021 (JP) ................................ 2021-100418

(51) Int. Cl.
*A61L 31/14* (2006.01)
*A61L 31/04* (2006.01)

(52) U.S. Cl.
CPC ............ *A61L 31/14* (2013.01); *A61L 31/041* (2013.01); *A61L 31/042* (2013.01); *A61L 31/043* (2013.01)

(58) Field of Classification Search
None
See application file for complete search history.

(56) References Cited

U.S. PATENT DOCUMENTS

2003/0105061 A1 6/2003 Ishikawa et al.
2015/0105336 A1 4/2015 Takamura et al.
2018/0021252 A1 1/2018 Delaney et al.
2018/0280587 A1 10/2018 Yano et al.
2020/0261355 A1* 8/2020 Morales Molina .. A61K 9/0019
2021/0369922 A1 12/2021 Yano et al.
2021/0393859 A1* 12/2021 Lee ......................... A61L 31/14
2022/0062498 A1* 3/2022 Ruane ..................... A61L 27/16

FOREIGN PATENT DOCUMENTS

| | | |
|---|---|---|
| EP | 2783709 | 10/2014 |
| JP | 2003201257 | 7/2003 |
| JP | 2019076391 | 5/2019 |
| JP | 2020189215 | 11/2020 |
| WO | 2013077357 | 5/2013 |
| WO | 2013133413 | 9/2013 |
| WO | 2017057504 | 4/2017 |

OTHER PUBLICATIONS

Par, Dig Dis Sci, 53, 2008 (Year: 2008).*
Tasuo Taniyada et al., "S1-09 Possibility of endoscopic treatment technique under D-sorbitol solution immersion for colorectal neoplastic lesions", Programs and Abstracts of the 11th Shikoku Division Regular Conference of the Japanese Society of Gastroenterology, Jun. 2019, with English translation thereof, pp. 41.
"International Search Report (Form PCT/ISA/210) of PCT/JP2022/018075", mailed on Jun. 21, 2022, with English translation thereof, pp. 1-7.
"Written Opinion of the International Searching Authority (Form PCT/ISA/237) of PCT/ JP2022/018075", mailed on Jun. 21, 2022, with English translation thereof, pp. 1-8.
"Notice of Reasons for Refusal of Japan Counterpart Application", issued on Feb. 10, 2026, with English translation thereof, p. 1-p. 6.

* cited by examiner

*Primary Examiner* — Susan T Tran
*Assistant Examiner* — William Craigo
(74) *Attorney, Agent, or Firm* — JCIPRNET

(57) ABSTRACT

An endoscopic submucosal injection material containing: a water-soluble resin having a weight-average molecular weight of 10,000 or more; an organic compound having two or more hydroxyl groups and having a molecular weight of 400 or less; and water is provided, in which the endoscopic submucosal injection material has an electrical conductivity of 500 mS/m or less, and an osmotic pressure ratio of the endoscopic submucosal injection material to physiological saline is 0.7 to 1.5.

9 Claims, No Drawings

ENDOSCOPIC SUBMUCOSAL INJECTION MATERIAL

CROSS-REFERENCE TO RELATED APPLICATION

This application is a Continuation of International Application No. PCT/JP2022/018075, filed Apr. 18, 2022, which claims priority to Japanese Patent Application No. 2021-100418, filed Jun. 16, 2021. Each of the above applications is hereby expressly incorporated by reference, in its entirety, into the present application.

BACKGROUND OF THE INVENTION

1. Field of the Invention

The present disclosure relates to an endoscopic submucosal injection material.

2. Description of the Related Art

Endoscopic mucosal resection (EMR) and endoscopic submucosal dissection (ESD) are known as treatment methods for gastrointestinal tract polyps, early gastric cancer, and early colorectal cancer (refer to Journal of the Japan Society of Coloproctology 66: 941-949, 2013).

In addition, in EMR or ESD, in order to facilitate resection, an endoscopic submucosal injection material is injected into a submucosal layer of a lesion area to elevate a mucous membrane below the lesion area, and thus, the endoscopic submucosal injection material is required to be excellent in elevation.

From the viewpoint of safety, an osmotic pressure of an endoscopic submucosal injection material is adjusted. For example, JP2003-201257A discloses an endoscopic submucosal injection material in which an osmotic pressure ratio to physiological saline is adjusted to 0.7 to 1.4.

Furthermore, WO2013/077357A discloses an endoscopic submucosal injection material containing an osmotic pressure-adjusting agent such as a sugar alcohol.

SUMMARY OF THE INVENTION

In EMR or ESD, a high-frequency knife is used for resection of a lesion area, but sparks are generated depending on endoscopic submucosal injection materials used, and because of a high-frequency knife being advanced in an unintended direction by a reaction to spark generation or because of the above-mentioned sparks, there is a risk of resecting a portion other than a lesion area. In addition, because a splash scattered by the above-mentioned sparks is adhered to an endoscope lens, there is a risk of a contamination of the endoscope lens.

In addition, the inventors of the present invention have found that there is room for improvement in ease of resection in the endoscopic submucosal injection materials disclosed in JP2003-201257A and WO2013/077357A because the above-mentioned sparks are generated, and there is a risk that resection cannot be easily performed.

The present disclosure has been made in view of the above-mentioned circumstances, and an object to be achieved thereof is to provide an endoscopic submucosal injection material which is excellent in safety, ease of resection, and elevation.

Specific means for achieving the object are as follows.

<1> An endoscopic submucosal injection material containing: a water-soluble resin having a weight-average molecular weight of 10,000 or more; an organic compound having two or more hydroxyl groups and having a molecular weight of 400 or less; and water, in which the endoscopic submucosal injection material has an electrical conductivity of 500 mS/m or less, and an osmotic pressure ratio of the endoscopic submucosal injection material to physiological saline is 0.7 to 1.5.

<2> The endoscopic submucosal injection material according to <1>, in which the organic compound includes one or more compounds selected from the group including a glycol compound, a sugar alcohol compound, a monosaccharide compound, and a disaccharide compound.

<3> The endoscopic submucosal injection material according to <1> or <2>, in which the organic compound includes one or more glycol compounds selected from the group consisting of propylene glycol, triethylene glycol, and polyethylene glycol.

<4> The endoscopic submucosal injection material according to <1> or <2>, in which the organic compound includes one or more sugar alcohol compounds selected from the group consisting of erythritol, glycerol, sorbitol, and xylitol.

<5> The endoscopic submucosal injection material according to any one of <1> to <4>, in which the molecular weight of the organic compound is 200 or less.

<6> The endoscopic submucosal injection material according to <1> or <2>, in which the organic compound includes one or more compounds selected from the group consisting of erythritol, glycerol, sorbitol, glucose, propylene glycol, triethylene glycol, and polyethylene glycol.

<7> The endoscopic submucosal injection material according to any one of <1> to <6>, in which the molecular weight of the organic compound is 100 or less.

<8> The endoscopic submucosal injection material according to any one of <1> to <7>, in which a content of the organic compound with respect to the endoscopic submucosal injection material is 1.9% by mass to 9.0% by mass.

<9> The endoscopic submucosal injection material according to any one of <1> to <8>, in which the water-soluble resin includes one or more compounds selected from the group consisting of a protein compound, a polysaccharide, and a derivative of these compounds.

<10> The endoscopic submucosal injection material according to any one of <1> to <9>, in which the water-soluble resin includes one or more compounds selected from the group consisting of sodium hyaluronate, xanthan gum, sodium carboxymethyl cellulose, locust bean gum, dextran, dextrin, sodium alginate, hydroxyalkyl cellulose, sodium carboxymethyl dextran, hydrophobized hydroxyalkyl cellulose, sodium poly(meth)acrylate, polyvinyl alcohol, gelatin, and casein.

<11> The endoscopic submucosal injection material according to any one of <1> to <10>, in which a content of the water-soluble resin with respect to the endoscopic submucosal injection material is 0.1% by mass to 1.5% by mass.

According to the present disclosure, an endoscopic submucosal injection material which is excellent in safety, ease of resection, and elevation can be provided.

DESCRIPTION OF THE PREFERRED EMBODIMENTS

In the present disclosure, a numerical value range shown using "to" includes numerical values written before and after "to" as a minimum value and a maximum value, respectively.

In a numerical value range described in a stepwise manner in the present disclosure, an upper limit value or a lower limit value described in one numerical value range may be replaced with an upper limit value or a lower limit value in another numerical value range described in a stepwise manner. Furthermore, in a numerical value range described in the present disclosure, an upper limit value or a lower limit value of this numerical value range may be replaced with values shown in examples.

In the present disclosure, an osmotic pressure is determined according to the 2.47 Osmolarity Determination (method for determining an osmotic concentration) of the Japanese Pharmacopoeia 17th Edition (Mar. 7, 2016, the Ministry of Health, Labour and Welfare Ministerial Notification No. 64) using an osmometer.

As the osmometer, an osmometer (OSMOMAT 300 (D) manufactured by Gonotec GmbH) or a similar device thereof can be used.

As physiological saline, a commercially available physiological saline having an osmotic pressure of 250 mOsmol/kg to 300 mOsmol/kg can be used.

As the commercially available physiological saline, OTSUKA NORMAL SALINE manufactured by Otsuka Pharmaceutical Factory, Inc. (osmotic pressure: 288 mOsmol/kg) can be used, for example.

The osmotic pressure ratio is obtained by dividing the measured osmotic pressure by the osmotic pressure value of the physiological saline.

In the present disclosure, electrical conductivity is measured using a conductivity meter with an endoscopic submucosal injection material set to 25° C.

As the conductivity meter, a pen type pH/conductivity meter MPC70 (manufactured by AS ONE Corporation) or a similar device thereof can be used.

In the present disclosure, a viscosity of the endoscopic submucosal injection material is measured using a rheometer under the condition of a frequency of 100 Hz with a temperature of the endoscopic submucosal injection material set to 25° C.

As the rheometer, it is possible to use a rheometer (manufactured by Anton Paar GmbH, automated rheometer MCR 102) to which a cone-plate jig (parallel plate, 10 mmΦ) is attached, or to use a similar device thereof.

In the present disclosure, a weight-average molecular weight (Mw) of a water-soluble resin having a weight-average molecular weight of 10,000 or more is a value obtained by determining using the following GPC determination device under the following determination conditions and converting using a calibration curve of polystyrene standards. In addition, the calibration curve is created using five sample sets ("PStQuick MP-H" and "PStQuick B", manufactured by Tosoh Corporation) as polystyrene standards.

GPC Determination Device

- GPC device: high speed GPC device "HCL-8320GPC", detector: differential refractometer or UV, manufactured by Tosoh Corporation
- Column: TSKgel SuperHZM-H, TSKgel SuperHZ4000, and TSKgel SuperHZ200 (all manufactured by Tosoh Corporation) which are connected in series in this order and used Determination Conditions

- Solvent: N-methylpyrrolidone (NMP)
- Column temperature: 40° C.

In the present disclosure, the molecular weight of an organic compound having two or more hydroxyl groups and having a molecular weight of 400 or less is obtained from the chemical structure of the compound, but in a case where the organic compound is a polymerized substance such as an oligomer, the molecular weight of the organic compound is determined using a GPC determination device under the above-mentioned determination conditions.

In the present disclosure, the term "water-soluble resin" refers to a resin having a solubility of 0.1 g or more in 100 g of water having a liquid temperature of 22° C. and a pH of 7.0.

In the present disclosure, the term "(meth)acrylic" means at least one of acryl or a methacrylic group.

<Endoscopic Submucosal Injection Material>

The endoscopic submucosal injection material of the present disclosure contains: a water-soluble resin having a weight-average molecular weight of 10,000 or more; an organic compound having two or more hydroxyl groups and having a molecular weight of 400 or less; and water, in which the endoscopic submucosal injection material has an electrical conductivity of 500 mS/m or less, and an osmotic pressure ratio of the endoscopic submucosal injection material to physiological saline is 0.7 to 1.5.

The endoscopic submucosal injection material of the present disclosure is excellent in ease of resection, safety, and elevation.

In the present disclosure, the endoscopic submucosal injection material excellent in safety refers to an endoscopic submucosal injection material capable of inhibiting induction of dehydration of tissue cells or cell death due to excessive uptake of water by tissue cells when the endoscopic submucosal injection material is injected into a submucosal layer.

The reason why the above-mentioned effects are obtained is presumed as follows, but is not limited thereto.

It is presumed that, since the endoscopic submucosal injection material of the present disclosure contains the water-soluble resin having a weight-average molecular weight of 10,000 or more and the organic compound having two or more hydroxyl groups and having a molecular weight of 400 or less, the electrical conductivity of the endoscopic submucosal injection material and the osmotic pressure ratio to physiological saline are set to favorable numerical values, thereby improving the ease of resection and the safety mentioned above.

In addition, in a case where the molecular weight of the above-mentioned organic compound is more than 400, it is required to increase the addition amount of the above-mentioned organic compound to improve the osmotic pressure of the endoscopic submucosal injection material of the present disclosure, which tends to cause a deterioration of ease of resection because a level difference is generated in a portion elevated by the injection of the endoscopic submucosal injection material. It is presumed that, since the organic compound, which has two or more hydroxyl groups and is contained in the endoscopic submucosal injection material of the present disclosure, has a molecular weight of 400 or less, the addition amount thereof can be reduced, which makes it possible to inhibit the deterioration of ease of resection caused by the above-mentioned level difference.

It is presumed that, since the endoscopic submucosal injection material contains the water-soluble resin having a weight-average molecular weight of 10,000 or more, the viscosity of the endoscopic submucosal injection material is increased, thereby improving elevation.

In addition, it is presumed that, since the electrical conductivity of the endoscopic submucosal injection material is 500 mS/m or less, the generation of sparks (scintillation by discharge) when using a high-frequency knife can be inhibited, thereby improving ease of resection.

In addition, it is presumed that, since the osmotic pressure ratio of the endoscopic submucosal injection material to physiological saline is 0.7 to 1.5, in a case where the endoscopic submucosal injection material is injected into the submucosal layer of a lesion area, movement of water between surrounding cells and the endoscopic submucosal injection material can be inhibited, thereby improving safety.

From the viewpoint of ease of resection, the electrical conductivity of the endoscopic submucosal injection material is preferably 100 mS/m or less, more preferably 50 mS/m or less, further preferably 10 mS/m or less, and particularly preferably 1 mS/m or less.

The lower limit value of the electrical conductivity is not particularly limited, but the lower the value is, the better it is. For example, the lower limit value thereof can be set to 0.1 mS/m or more.

The electrical conductivity of the endoscopic submucosal injection material can be adjusted by changing the type and the content of the water-soluble resin having a weight-average molecular weight of 10,000 or more and the organic compound having two or more hydroxyl groups and having a molecular weight of 400 or less.

From the viewpoint of safety, the osmotic pressure ratio of the endoscopic submucosal injection material to physiological saline is more preferably 0.8 to 1.3, and further preferably 0.9 to 1.1.

The osmotic pressure ratio of the endoscopic submucosal injection material to physiological saline can be adjusted by changing the type and the content of the water-soluble resin having a weight-average molecular weight of 10,000 or more and the organic compound having two or more hydroxyl groups and having a molecular weight of 400 or less.

From the viewpoint of safety, as the amount of endotoxin in the endoscopic submucosal injection material becomes smaller, it becomes more preferable. Specifically, the amount thereof is preferably 50 EU/mL or less.

In the present disclosure, the amount of endotoxin is detected according to the gelling method of the Japanese Pharmacopoeia 17th Edition (Mar. 7, 2016, the Ministry of Health, Labour and Welfare Ministerial Notification No. 64). A Limulus Color KY Test Wako is used as an endotoxin detection reagent, and a Japanese Pharmacopoeia endotoxin reference standard is used as an endotoxin reference standard.

From the viewpoint of elevation and ease of injection, the viscosity of the endoscopic submucosal injection material at 25° C. is preferably 10 mPa·s to 500 mPa·s, and more preferably 50 mPa·s to 200 mPa·s.

(Water-Soluble Resin Having Weight-Average Molecular Weight of 10,000 or More)

The endoscopic submucosal injection material of the present disclosure contains the water-soluble resin having a weight-average molecular weight of 10,000 or more (hereinafter, also referred to as a specific water-soluble resin).

From the viewpoint of elevation, the weight-average molecular weight of the specific water-soluble resin is preferably 10,000 or more, and more preferably 100,000 or more.

The upper limit value of the weight-average molecular weight of the specific water-soluble resin is not particularly limited, but from the viewpoint of ease of injection, the upper limit value thereof is preferably 10,000,000 or less, more preferably 5,000,000 or less, and further preferably 2,000,000 or less.

From the viewpoint of ease of resection, safety, and elevation, the specific water-soluble resin preferably includes one or more compounds selected from the group consisting of a protein compound, a polysaccharide, and a derivative thereof. The term derivative means a compound in which a part of the structure has been modified (change of substituent, introduction of sub stituent, or the like) while maintaining the basic skeleton of the compound.

Examples of the protein compounds include casein, albumin, methylated collagen, hydrolyzed collagen, water-soluble collagen, gelatin, and a synthetic peptide.

Examples of the polysaccharides include hyaluronic acid, sodium hyaluronate, xanthan gum, sodium carboxymethyl cellulose, locust bean gum, dextran, dextrin, sodium alginate, hydroxyalkyl cellulose (hydroxypropyl methylcellulose and the like), sodium carboxymethyl dextran, hydrophobized hydroxyalkyl cellulose, sodium poly(meth) acrylate, polyvinyl alcohol, arabic gum, tragacanth gum, karaya gum, tamarind gum, guar gum, gellan gum, and sodium chondroitin sulfate.

From the viewpoint of ease of resection, safety, and elevation, among the above-mentioned examples, the specific water-soluble resin preferably includes one or more compounds selected from the group consisting of sodium hyaluronate, xanthan gum, sodium carboxymethyl cellulose, locust bean gum, dextran, dextrin, sodium alginate, hydroxyalkyl cellulose, sodium carboxymethyl dextran, hydrophobized hydroxyalkyl cellulose, sodium poly(meth) acrylate, polyvinyl alcohol, gelatin, and casein; more preferably includes one or more compounds selected from the group consisting of xanthan gum, locust bean gum, hydrophobized hydroxyalkyl cellulose, and sodium poly(meth) acrylate; and further preferably includes hydrophobized hydroxyalkyl cellulose.

The sodium poly(meth)acrylate may have a crosslinking structure or may not have a crosslinking structure.

From the viewpoint of ease of resection, safety, elevation, elevation sustainability, ease of injection, and the like, the above-mentioned hydrophobized hydroxyalkyl cellulose is preferably represented by General Formula (1) below.

(1)

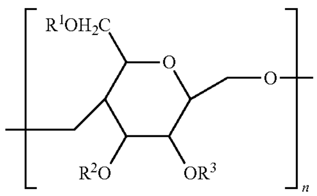

In General Formula (1), $R^1$, $R^2$, and $R^3$ each independently represent a hydrogen atom, an alkyl group having 1 to 4 carbon atoms, $—[CH_2CH_{2-k}(CH_3)_kO]_mH$, or $—CH_2CH(OH)CH_2OC_jH_{2j+1}$.

The hydrophobized hydroxyalkyl cellulose represented by General Formula (1) has at least one $—CH_2CH(OH)CH_2OC_jH_{2j+1}$.

In addition, in a case where n is 2 or more, two or more $R^1$'s and the like may be the same as or different from each other.

The alkyl group having 1 to 4 carbon atoms may be linear or branched. Examples of the alkyl groups having 1 to 4 carbon atoms include a methyl group, an ethyl group, a propyl group, an isopropyl group, a butyl group, an isobutyl group, and t-butyl group.

The content of the alkyl group having 1 to 4 carbon atoms with respect to the mass of the hydrophobized hydroxyalkyl cellulose represented by General Formula (1) is preferably 10% by mass to 50% by mass.

In $—[CH_2CH_{2-k}(CH_3)_kO]_mH$, k represents 0 or 1. In addition, m represents an integer of 1 to 10, preferably an integer of 1 to 5, and more preferably 1.

The content of $—[CH_2CH_{2-k}(CH_3)_kO]_mH$ with respect to the mass of the hydrophobized hydroxyalkyl cellulose represented by General Formula (1) is preferably 3% by mass to 20% by mass.

In $—CH_2CH(OH)CH_2OC_jH_{2j+1}$, j represents an integer of 6 to 26, and from the viewpoint of ease of resection, safety, elevation, elevation sustainability, ease of injection, and the like, j preferably represents an integer of 10 to 20, and more preferably represents an integer of 15 to 18.

From the viewpoint of ease of resection, safety, elevation, elevation sustainability, ease of injection, and the like, the content of $—CH_2CH(OH)CH_2OC_jH_{2j+1}$ with respect to the mass of the hydrophobized hydroxyalkyl cellulose represented by General Formula (1) is preferably 0.1% by mass to 10% by mass, more preferably 0.2% by mass to 1.0% by mass, and further preferably 0.3% by mass to 0.6% by mass.

In General Formula (1), n represents an integer of 100 to 100,000, preferably represents an integer of 100 to 10,000, and more preferably represents an integer of 2,000 to 4,000.

Mw of the hydrophobized hydroxyalkyl cellulose represented by General Formula (1) is preferably 10,000 to 10,000,000, more preferably 50,000 to 5,000,000, and further preferably 100,000 to 1,000,000.

Examples of the hydrophobized hydroxyalkyl cellulose satisfying General Formula (1) include palmitoylated hydroxypropyl methylcellulose, margarylated hydroxypropyl methylcellulose, and stearylated hydroxypropyl methylcellulose.

The hydrophobized hydroxyalkyl celluloses satisfying General Formula (1) preferably include stearylated hydroxypropyl methylcellulose from the viewpoint of ease of resection, safety, elevation, elevation sustainability, ease of injection, and the like.

The hydrophobized hydroxyalkyl cellulose represented by General Formula (1) may be one manufactured by a conventionally known method or may be commercially available one.

Examples of commercially available products include SANGELOSE (registered trademark) 90L and SANGELOSE (registered trademark) 60L which are manufactured by Daido Chemical Corporation.

From the viewpoint of ease of resection, safety, and elevation, the content of the specific water-soluble resin with respect to the mass of the endoscopic submucosal injection material is preferably 0.1% by mass to 1.5% by mass, and more preferably 0.3% by mass to 1.3% by mass.

In a case where the specific water-soluble resin includes a hydrophobized hydroxyalkyl cellulose, the content of the hydrophobized hydroxyalkyl cellulose with respect to the mass of the endoscopic submucosal injection material is preferably 0.1% by mass to 0.5% by mass, and more preferably 0.2% by mass to 0.4% by mass from the viewpoint of ease of resection, safety, and elevation.

In a case where the specific water-soluble resin includes one or more compounds selected from the group consisting of sodium hyaluronate, sodium poly(meth)acrylate, xanthan gum, sodium carboxymethyl cellulose, locust bean gum, sodium alginate, and sodium carboxymethyl dextran, the sum of the contents of these with respect to the mass of the endoscopic submucosal injection material is preferably 0.1% by mass to 0.9% by mass, and more preferably 0.1% by mass to 0.6% by mass from the viewpoint of ease of resection, safety, and elevation.

In a case where the specific water-soluble resin includes one or more compounds selected from the group consisting of dextran, dextrin, hydroxyalkyl cellulose, polyvinyl alcohol, gelatin, and casein, the sum of the contents of these with respect to the mass of the endoscopic submucosal injection material is preferably 0.5% by mass to 1.5% by mass, and more preferably 0.8% by mass to 1.3% by mass from the viewpoint of ease of resection, safety, and elevation.

Organic Compound Having Two or More Hydroxyl Groups and Having Molecular Weight of 400 or Less The endoscopic submucosal injection material of the present disclosure contains the organic compound having two or more hydroxyl groups and having a molecular weight of 400 or less (hereinafter, also referred to as a specific organic compound).

From the viewpoint of ease of resection, the molecular weight of the specific organic compound is preferably 200 or less, and more preferably 100 or less.

The upper limit value of the molecular weight of the specific organic compound is not particularly limited, but can be 50 or more, for example.

From the viewpoint of ease of resection and safety, the specific organic compound preferably includes one or more compounds selected from the group including a glycol compound, a sugar alcohol compound, a monosaccharide compound, and a disaccharide compound.

Examples of the glycol compounds include propylene glycol, triethylene glycol, and polyethylene glycol.

Examples of the sugar alcohol compounds include erythritol, glycerol, sorbitol, and xylitol.

Examples of the monosaccharide compounds include glucose, mannose, galactose, and fructose.

Examples of the disaccharide compounds include sucrose, lactose, lactulose, maltose, and trehalose.

From the viewpoint of ease of resection and safety, the specific organic compound preferably includes one or more compounds selected from the group consisting of erythritol, glycerol, sorbitol, glucose, propylene glycol, triethylene glycol, and polyethylene glycol.

The content of the specific organic compound with respect to the mass of the endoscopic submucosal injection material is preferably 1.9% by mass to 9.0% by mass, and more preferably 2.1% by mass to 5.7% by mass.

In a case where the content of the specific organic compound is within the above-mentioned numerical value range, ease of resection and safety can be further improved.

(Water)

Examples of the water include ion exchange water, pure water, and purified water, among which pure water or purified water is preferable from the viewpoint of applicability to the endoscopic submucosal injection material.

In addition, purified water in which sodium chloride, an organic compound, or the like has been dispersed or dissolved, or the like may be used.

The content of water with respect to the mass of the endoscopic submucosal injection material is not particularly limited, and can be 80% by mass to 99.9% by mass, for example.

(Other)

The endoscopic submucosal injection material of the present disclosure may contain an osmotic pressure-adjusting agent, such as sodium chloride, sodium dihydrogen phosphate, and disodium hydrogen phosphate, a coloring agent, a contrast medium, a filling material, a cancer therapeutic agent, a hormone agent, an anti-inflammatory agent, an antibiotic, an analgesic drug, an antibacterial agent, a pH adjusting agent, or the like.

(Therapeutic Method)

In a therapeutic method of the present disclosure, the endoscopic submucosal injection material is injected into the submucosal layer of a lesion area to elevate a mucous membrane below the lesion area, and the above-mentioned lesion area is resected.

The injection of the endoscopic submucosal injection material into the submucosal layer of the lesion area can be carried out by a conventionally known method used in EMR or ESD, and can be carried out using an endoscopic puncture needle, for example.

Examples of the endoscopic puncture needle include Super Grip manufactured by TOP Corporation.

The resection of a lesion area can be carried out by a conventionally known method used in EMR or ESD, and can be carried out using a high-frequency knife, for example.

Examples of the high-frequency knife include a disposable high-frequency knife FlushKnife BT-S DK2620J manufactured by FUJIFILM Corporation.

Vibration can be applied to the above-mentioned high-frequency knife by a high-frequency device, and examples of the high-frequency device include ERBE ICC 200 manufactured by AMCO INC.

EXAMPLES

Hereinafter, the above-mentioned embodiment will be specifically described with reference to examples, but the above-mentioned embodiment is not limited to these examples.

Example 1 to Example 37

A water-soluble resin having a weight-average molecular weight of 10,000 or more (described as Specific water-soluble resin in the tables), an organic compound having two or more hydroxyl groups and having a molecular weight of 400 or less (described as Specific organic compound in the tables), pure water, and the like were blended according to the compositions shown in Tables 1 to 3 to prepare endoscopic submucosal injection materials.

As a result of detecting the amount of endotoxin in the endoscopic submucosal injection material prepared in Example 10 according to the gelling method of the Japanese Pharmacopoeia 17th Edition (Mar. 7, 2016, the Ministry of Health, Labour and Welfare Ministerial Notification No. 64) using a Limulus Color KY Test Wako as an endotoxin detection reagent and using a Japanese Pharmacopoeia endotoxin reference standard as an endotoxin reference standard, the amount thereof was 0.0005 EU/mL or less (detection limit or less).

As a result of measuring the viscosities of the endoscopic submucosal injection materials of Example 1 and Example 10 using a rheometer under the condition of a frequency of 100 Hz with the temperature of the endoscopic submucosal injection material set to 25° C., the viscosities thereof were 49 mPa·s and 95 mPa·s, respectively.

As the rheometer, a rheometer (manufactured by Anton Paar GmbH, automated rheometer MCR 102) to which a cone-plate jig (parallel plate, 10 mmΦ) had been attached was used.

Comparative Example 1 and Comparative Example 2

Sodium chloride and pure water were blended according to the compositions shown in Table 4 to prepare endoscopic submucosal injection materials. As a result of measuring the viscosity of the endoscopic submucosal injection material of Comparative Example 1 using a rheometer under the condition of a frequency of 100 Hz with the temperature of the endoscopic submucosal injection material set to 25° C., the viscosity thereof was 1 mPa·s.

Comparative Example 3

An endoscopic submucosal injection material was prepared in the same manner as in Example 1 except that an organic compound having two or more hydroxyl groups and having a molecular weight of 400 or less was not used.

Comparative Example 4

An organic compound having two or more hydroxyl groups and having a molecular weight of 400 or less and pure water were blended according to the composition shown in Table 4 to prepare an endoscopic submucosal injection material.

Comparative Example 5

A water-soluble resin having a weight-average molecular weight of 10,000 or more, an organic compound having two or more hydroxyl groups and having a molecular weight of 400 or less, and pure water were blended according to the composition shown in Table 4 to prepare an endoscopic submucosal injection material.

Comparative Example 6

A water-soluble resin having a weight-average molecular weight of 10,000 or more, an organic compound having two or more hydroxyl groups and having a molecular weight of more than 400, and pure water were blended according to the composition shown in Table 4 to prepare an endoscopic submucosal injection material.

Comparative Example 7

A water-soluble resin having a weight-average molecular weight of 10,000 or more, sodium chloride, sodium dihydrogen phosphate, disodium hydrogen phosphate, and pure water were blended according to the composition shown in Table 4 to prepare an endoscopic submucosal injection material.

Comparative Example 8

An endoscopic submucosal injection material was prepared in the same manner as in Example 1 except that a water-soluble resin having a weight-average molecular weight of 10,000 or more was not used.

As a result of measuring the viscosity of the endoscopic submucosal injection material of Comparative Example 8 using a rheometer under the condition of a frequency of 100 Hz with the temperature of the endoscopic submucosal injection material set to 25° C., the viscosity thereof was 10 mPa·s.

Comparative Example 9

An endoscopic submucosal injection material was prepared in the same manner as in Example 1 except that sodium hyaluronate A (manufactured by FUJIFILM Wako Pure Chemical Corporation, Mw: 1,000,000) as a water-soluble resin having a weight-average molecular weight of 10,000 or more was changed to sodium hyaluronate B (manufactured by Kewpie Corporation, Hyalonano (registered trademark), Mw: 2,000) as a water-soluble resin having a weight-average molecular weight of less than 10,000.

Details of the various materials shown in Table 1 to Table 4 are as follows.

<Water-Soluble Resin Having Weight-Average Molecular Weight of 10,000 or More>

- Sodium hyaluronate A: manufactured by FUJIFILM Wako Pure Chemical Corporation, Mw: 1,000,000
- Xanthan gum: manufactured by FUJIFILM Wako Pure Chemical Corporation
- Sodium carboxymethyl cellulose: manufactured by Sigma-Aldrich Co., LLC., Mw: 250,000
- Locust bean gum: manufactured by FUJIFILM Wako Pure Chemical Corporation, Mw>10,000
- Dextran: manufactured by FUJIFILM Wako Pure Chemical Corporation, Dextran 150,000, Mw: 150,000
- Dextrin: manufactured by FUJIFILM Wako Pure Chemical Corporation, Dextrin Hydrate, MW>10,000
- Sodium alginate: manufactured by FUJIFILM Wako Pure Chemical Corporation, Sodium Alginate 300-400, Mw: 63,000
- Hydroxypropyl methylcellulose: manufactured by Sigma-Aldrich Co., LLC., Mw: 120,000
- Sodium carboxymethyl dextran: manufactured by Meito Sangyo Co., Ltd., CMD-500, Mw: 500,000
- Stearylated hydroxypropyl methylcellulose: manufactured by Daido Chemical Corporation, SANGELOSE (registered trademark) 90L, the hydrophobized hydroxyalkyl cellulose satisfying General Formula (1) above, Mw: 700,000 to 900,000, content of $-CH_2CH(OH)CH_2OC_jH_{2j+1}$: 0.3% by mass to 0.6% by mass
- Sodium polyacrylate: manufactured by FUJIFILM Wako Pure Chemical Corporation, degree of polymerization: 22,000 to 70,000
- Crosslinked sodium polyacrylate: manufactured by FUJIFILM Wako Pure Chemical Corporation, HIVISWAKO 104, MW>10,000
- Polyvinyl alcohol: manufactured by FUJIFILM Wako Pure Chemical Corporation, degree of saponification: 78 mol % to 82 mol %, MW>10,000
- Gelatin: manufactured by FUJIFILM Wako Pure Chemical Corporation, MW>10,000
- Casein: manufactured by FUJIFILM Wako Pure Chemical Corporation, derived from milk, MW>10,000

<Organic Compound Having Two or More Hydroxyl Groups and Having Molecular Weight of 400 or Less>

- Glycerol: manufactured by FUJIFILM Wako Pure Chemical Corporation, reagent specific grade, molecular weight: 92
- Erythritol: manufactured by FUJIFILM Wako Pure Chemical Corporation, meso-Erythritol, Wako 1st grade, molecular weight: 122
- Sorbitol: manufactured by FUJIFILM Wako Pure Chemical Corporation, D(−)-Sorbitol, Wako 1st grade, molecular weight: 182
- Xylitol: manufactured by FUJIFILM Wako Pure Chemical Corporation, Wako special grade, molecular weight: 152
- Propylene glycol: manufactured by FUJIFILM Wako Pure Chemical Corporation, guaranteed reagent, molecular weight: 76
- Triethylene glycol: manufactured by FUJIFILM Wako Pure Chemical Corporation, molecular weight: 150
- Polyethylene glycol 200: manufactured by FUJIFILM Wako Pure Chemical Corporation, Wako 1st grade, Mw: 200 (oligomer, where the weight-average molecular weight was measured with a GPC determination device)
- Glucose: manufactured by FUJIFILM Wako Pure Chemical Corporation, D(+)-Glucose, guaranteed reagent, molecular weight: 180
- Mannose: manufactured by FUJIFILM Wako Pure Chemical Corporation, D(+)-Mannose, Wako special grade, molecular weight: 180
- Galactose: manufactured by FUJIFILM Wako Pure Chemical Corporation, D(+)-Galactose, Wako special grade, molecular weight: 180
- Fructose: manufactured by FUJIFILM Wako Pure Chemical Corporation, D(−)-Fructose, Wako special grade, molecular weight: 180
- Sucrose: manufactured by FUJIFILM Wako Pure Chemical Corporation, guaranteed reagent, molecular weight: 342
- Lactose: manufactured by FUJIFILM Wako Pure Chemical Corporation, Lactose Hydrate, reagent specific grade, molecular weight: 342
- Maltose: manufactured by FUJIFILM Wako Pure Chemical Corporation, Maltose Hydrate, reagent specific grade, molecular weight: 342
- Trehalose: manufactured by FUJIFILM Wako Pure Chemical Corporation, Wako special grade, molecular weight: 342
- Mannitol: manufactured by FUJIFILM Wako Pure Chemical Corporation, D(−)-Mannitol, guaranteed reagent, molecular weight: 342

<Others>

- Polyethylene glycol 600: manufactured by FUJIFILM Wako Pure Chemical Corporation, Wako 1st grade, Mw: 600
- Sodium dihydrogen phosphate: manufactured by FUJIFILM Wako Pure Chemical Corporation, Wako special grade
- Disodium hydrogen phosphate: manufactured by FUJIFILM Wako Pure Chemical Corporation, Wako special grade
- Sodium chloride: manufactured by FUJIFILM Wako Pure Chemical Corporation, guaranteed reagent
- Sodium hyaluronate B: manufactured by Kewpie Corporation, Hyalonano (registered trademark), Mw: 2,000

<Measurement of Electrical Conductivity>

The measurement was carried out using a pen type pH/conductivity meter MPC70 (manufactured by AS ONE Corporation) with the endoscopic submucosal injection materials prepared in the above-mentioned examples and comparative examples set to 25° C. The measurement results are summarized in Table 1 to Table 4.

<Measurement of Osmotic Pressure Ratio to Physiological Saline>

The osmotic pressures of the endoscopic submucosal injection materials prepared in the above-mentioned examples and comparative examples were determined according to the 2.47 Osmolarity Determination (method for determining an osmotic concentration) of the Japanese Pharmacopoeia 17th Edition (Mar. 7, 2016, the Ministry of Health, Labour and Welfare Ministerial Notification No. 64) using an osmometer (manufactured by Gonotec GmbH, OSMOMAT 300 (D)). The measured osmotic pressure was divided by the osmotic pressure value of OTSUKA NORMAL SALINE to obtain the osmotic pressure ratio. The measurement results are summarized in Table 1 to Table 4.

As physiological saline, OTSUKA NORMAL SALINE (manufactured by Otsuka Pharmaceutical Factory, Inc., osmotic pressure 288 mOsmol/kg) was used.

<Evaluation of Ease of Resection>

An upper part (the upper part when the total length was divided into three equal parts) of an excised pig stomach was cut into a 5-cm square to produce a test piece.

2 mL of each of the endoscopic submucosal injection materials prepared in the examples and the comparative examples was injected into the submucosal layer of the test piece using an endoscopic puncture needle (manufactured by TOP Corporation, Super Grip; needle gauge: 23 G) to elevate a mucosal layer.

The elevated mucosal layer was resected with a high-frequency incision tool (manufactured by FUJIFILM Corporation, a disposable high-frequency knife, FlushKnife BT-S DK2620J).

In the case of the resection of the mucosal layer, vibration was applied to the high-frequency incision tool by a high-frequency device (manufactured by AMCO INC., ERBE ICC 200) set in "Swift Coagulation, effect 4, 40 W".

The number of resection operations (swings) in one direction required for the resection of the mucosal layer was measured and evaluated based on the following evaluation standards. The evaluation results are summarized in Table 1 to Table 4.

(Evaluation Standards)

A: No sparks were generated, and the number of resection operations was 4 or less.

B: A small amount of sparks were generated, and the number of resection operations was more than 4 and equal to or less than 7.

C: Sparks were generated, and the number of resection operations was more than 7 and equal to or less than 9, which was within a range of no problems in practical use.

D: Sparks were generated, and the number of resection operations was more than 9 and equal to or less than 15, which was a problem in practical use.

E: Sparks were generated, and the number of resection operations was more than 15.

<Evaluation of Safety>

The excised small intestine of the pig was cut open and washed with physiological saline to remove excess water, thereby producing a test piece of 3 cm×3 cm×1 mm.

50 mL of each of the endoscopic submucosal injection materials prepared in the examples and the comparative examples was prepared, and the above-mentioned test piece was immersed in the endoscopic submucosal injection material for 24 hours at 25° C.

After the immersion, the excess solution was lightly wiped off to measure the mass of the test piece, and the mass change rates of the test piece (mass of test piece after immersion/mass of test piece before immersion×100) were calculated and summarized in Table 1 to Table 4.

In a case where the endoscopic submucosal injection material with a mass change rate of less than 85% is injected into the submucosal layer, there is a risk of the occurrence of dehydration of tissue cells, which is a concern for safety.

In a case where the endoscopic submucosal injection material with a mass change rate of more than 120% is injected into the submucosal layer, there is a risk of cell death due to excessive uptake of water by tissue cells, which is a concern for safety.

Therefore, from the viewpoint of safety, the endoscopic submucosal injection material with a mass change rate of 85% to 120% is preferable.

<Evaluation of Elevation>

The upper part (the upper part when the total length was divided into three equal parts) of the excised pig stomach was cut into a 5-cm square to produce a test piece.

2 mL of each of the endoscopic submucosal injection materials prepared in the examples and the comparative examples was injected into the submucosal layer of the test piece using an endoscopic puncture needle (manufactured by TOP Corporation, Super Grip; needle gauge: 23 G).

The height of the elevation of the mucosal layer 30 minutes after the injection was measured and evaluated based on the following evaluation standards. The evaluation results are summarized in Table 1.

Regarding the measurement of the height of the elevation, the maximum height of the elevation was gauged using a laser displacement sensor IX-150 (manufactured by KEYENCE CORPORATION) with a built-in camera.

(Evaluation Standards)

A: The height of the elevation was 10 mm or more.

B: The height of the elevation was equal to or more than 8 mm and less than 10 mm.

C: The height of the elevation was equal to or more than 5 mm and less than 8 mm.

D: The height of the elevation was equal to or more than 2 mm and less than 5 mm.

E: The height of the elevation was less than 2 mm.

TABLE 1

| | | | Example 1 | Example 2 | Example 3 | Example 4 | Example 5 | Example 6 | Example 7 | Example 8 |
|---|---|---|---|---|---|---|---|---|---|---|
| Composition (parts by mass) | Specific water-soluble resin | Sodium hyaluronate A | 0.4 | — | — | — | — | — | — | — |
| | | Xanthan gum | — | 0.5 | — | — | — | — | — | — |
| | | Sodium carboxymethyl cellulose | — | — | 0.5 | — | — | — | — | — |
| | | Locust bean gum | — | — | — | 0.5 | — | — | — | — |
| | | Dextran | — | — | — | — | 1 | — | — | — |
| | | Dextrin | — | — | — | — | — | 1 | — | — |
| | | Sodium alginate | — | — | — | — | — | — | 0.6 | — |

TABLE 1-continued

| | | | | | | | | | | |
|---|---|---|---|---|---|---|---|---|---|---|
| | | Hydroxypropyl methylcellulose | — | — | — | — | — | — | — | 1 |
| | | Sodium carboxymethyl dextran | — | — | — | — | — | — | — | — |
| | | Stearylated hydroxy propyl methylcellulose | — | — | — | — | — | — | — | — |
| | | Sodium polyacrylate | — | — | — | — | — | — | — | — |
| | | Crosslinked sodium polyacrylate | — | — | — | — | — | — | — | — |
| | | Polyvinyl alcohol | — | — | — | — | — | — | — | — |
| | | Gelatin | — | — | — | — | — | — | — | — |
| | | Casein | — | — | — | — | — | — | — | — |
| | Specific organic compound | Glycerol | 2.6 | 2.6 | 2.6 | 2.6 | 2.6 | 2.6 | 2.6 | 2.6 |
| | Pure water | | 95 | 95 | 95 | 95 | 95 | 95 | 95 | 95 |
| Physical property value | | Electrical conductivity (mS/m) | 40 | 15 | 120 | 0.6 | 0.5 | 0.6 | 130 | 0.6 |
| | | Osmotic pressure ratio to physiological saline | 1.1 | 1 | 1 | 1 | 1 | 1 | 1.2 | 1 |
| Evaluation | | Evaluation of ease of resection | A | A | B | A | A | A | B | A |
| | | Evaluation of safety (mass change rate) | 101% | 102% | 99% | 101% | 101% | 102% | 103% | 104% |
| | | Evaluation of elevation | C | B | B | B | B | C | C | C |

| | | | Example 9 | Example 10 | Example 11 | Example 12 | Example 13 | Example 14 | Example 15 |
|---|---|---|---|---|---|---|---|---|---|
| Composition (parts by mass) | Specific water-soluble resin | Sodium hyaluronate A | — | — | — | — | — | — | — |
| | | Xanthan gum | — | — | — | — | — | — | — |
| | | Sodium carboxymethyl cellulose | — | — | — | — | — | — | — |
| | | Locust bean gum | — | — | — | — | — | — | — |
| | | Dextran | — | — | — | — | — | — | — |
| | | Dextrin | — | — | — | — | — | — | — |
| | | Sodium alginate | — | — | — | — | — | — | — |
| | | Hydroxypropyl methylcellulose | — | — | — | — | — | — | — |
| | | Sodium carboxymethyl dextran | 0.5 | — | — | — | — | — | — |
| | | Stearylated hydroxy propyl methylcellulose | — | 0.3 | — | — | — | — | — |
| | | Sodium polyacrylate | — | — | 0.3 | — | — | — | — |
| | | Crosslinked sodium polyacrylate | — | — | — | 0.1 | — | — | — |
| | | Polyvinyl alcohol | — | — | — | — | 1 | — | — |
| | | Gelatin | — | — | — | — | — | 1 | — |
| | | Casein | — | — | — | — | — | — | 1 |
| | Specific organic compound | Glycerol | 2.6 | 2.6 | 2.6 | 2.6 | 2.6 | 2.6 | 2.6 |
| | Pure water | | 95 | 95 | 95 | 95 | 95 | 95 | 95 |
| Physical property value | | Electrical conductivity (mS/m) | 110 | 0.6 | 140 | 50 | 0.6 | 220 | 140 |
| | | Osmotic pressure ratio to physiological saline | 1.1 | 1 | 1.1 | 1.1 | 1 | 1 | 1 |
| Evaluation | | Evaluation of ease of resection | B | A | B | B | A | B | B |
| | | Evaluation of safety (mass change rate) | 98% | 100% | 99% | 101% | 101% | 100% | 97% |
| | | Evaluation of elevation | B | A | A | A | C | C | C |

TABLE 2

| | | | Example 16 | Example 17 | Example 18 | Example 19 | Example 20 | Example 21 |
|---|---|---|---|---|---|---|---|---|
| Composition (parts by mass) | Specific water-soluble resin | Stearylated hydroxypropyl methylcellulose | 0.3 | 0.3 | 0.3 | 0.3 | 0.3 | 0.3 |
| | Specific organic compound | Glycerol | 1.9 | 2.1 | 3.2 | 3.9 | 2.6 | 2.6 |
| | | Erythritol | — | — | — | — | — | — |
| | | Sorbitol | — | — | — | — | — | — |
| | | Xylitol | — | — | — | — | — | — |
| | | Propylene glycol | — | — | — | — | — | — |
| | Others | Sodium dihydrogen phosphate | — | — | — | — | 0.0035 | 0.007 |
| | | Disodium hydrogen phosphate | — | — | — | — | 0.0103 | 0.0206 |
| | Pure water | | 95 | 95 | 95 | 95 | 95 | 95 |
| Physical property value | | Electrical conductivity (mS/m) | 0.5 | 0.5 | 0.5 | 0.5 | 115 | 230 |
| | | Osmotic pressure ratio to physiological saline | 0.7 | 0.8 | 1.2 | 1.5 | 1.1 | 1.2 |
| Evaluation | | Evaluation of ease of resection | A | A | A | A | B | B |
| | | Evaluation of safety (mass change rate) | 110% | 108% | 93% | 90% | 98% | 95% |
| | | Evaluation of elevation | A | A | A | A | A | A |

| | | | Example 22 | Example 23 | Example 24 | Example 25 | Example 26 |
|---|---|---|---|---|---|---|---|
| Composition (parts by mass) | Specific water-soluble resin | Stearylated hydroxypropyl methylcellulose | 0.3 | 0.3 | 0.3 | 0.3 | 0.3 |
| | Specific organic compound | Glycerol | 2.6 | — | — | — | — |
| | | Erythritol | — | 3.4 | — | — | — |
| | | Sorbitol | — | — | 5.1 | — | — |
| | | Xylitol | — | — | — | 4.3 | — |
| | | Propylene glycol | — | — | — | — | 2.1 |
| | Others | Sodium dihydrogen phosphate | 0.028 | — | — | — | — |
| | | Disodium hydrogen phosphate | 0.0824 | — | — | — | — |
| | Pure water | | 95 | 95 | 95 | 95 | 95 |
| Physical property value | | Electrical conductivity (mS/m) | 460 | 0.5 | 0.6 | 0.5 | 0.6 |
| | | Osmotic pressure ratio to physiological saline | 1.4 | 1 | 1 | 1 | 1 |
| Evaluation | | Evaluation of ease of resection | C | A | A | A | A |
| | | Evaluation of safety (mass change rate) | 88% | 99% | 100% | 101% | 102% |
| | | Evaluation of elevation | A | A | A | A | A |

TABLE 3

| | | | Example 27 | Example 28 | Example 29 | Example 30 | Example 31 | Example 32 |
|---|---|---|---|---|---|---|---|---|
| Composition (parts by mass) | Specific water-soluble resin | Stearylated hydroxypropyl methylcellulose | 0.3 | 0.3 | 0.3 | 0.3 | 0.3 | 0.3 |
| | Specific organic compound | Triethylene glycol | 3.0 | — | — | — | — | — |
| | | Polyethylene glycol 200 | — | 5.6 | — | — | — | — |
| | | Glucose | — | — | 5.1 | — | — | — |
| | | Mannose | — | — | — | 5.1 | — | — |
| | | Galactose | — | — | — | — | 5.1 | — |
| | | Fructose | — | — | — | — | — | 5.1 |
| | | Sucrose | — | — | — | — | — | — |
| | | Lactose | — | — | — | — | — | — |
| | | Maltose | — | — | — | — | — | — |
| | | Trehalose | — | — | — | — | — | — |
| | | Mannitol | — | — | — | — | — | — |
| | Pure water | | 95 | 95 | 95 | 95 | 95 | 95 |
| Physical property value | | Electrical conductivity (mS/m) | 0.5 | 0.5 | 0.6 | 0.5 | 0.5 | 0.6 |
| | | Osmotic pressure ratio to physiological saline | 1 | 1 | 1 | 1 | 1 | 1 |
| Evaluation | | Evaluation of ease of resection | A | A | A | A | A | A |
| | | Evaluation of safety (mass change rate) | 100% | 99% | 100% | 103% | 99% | 100% |
| | | Evaluation of elevation | A | A | A | A | A | A |

| | | | Example 33 | Example 34 | Example 35 | Example 36 | Example 37 |
|---|---|---|---|---|---|---|---|
| Composition (parts by mass) | Specific water-soluble resin | Stearylated hydroxypropyl methylcellulose | 0.3 | 0.3 | 0.3 | 0.3 | 0.3 |
| | Specific organic compound | Triethylene glycol | — | — | — | — | — |
| | | Polyethylene glycol 200 | — | — | — | — | — |
| | | Glucose | — | — | — | — | — |
| | | Mannose | — | — | — | — | — |
| | | Galactose | — | — | — | — | — |
| | | Fructose | — | — | — | — | — |

TABLE 3-continued

| | | | | | | | |
|---|---|---|---|---|---|---|---|
| | | Sucrose | 9.7 | — | — | — | — |
| | | Lactose | — | 9.7 | — | — | — |
| | | Maltose | — | — | 9.7 | — | — |
| | | Trehalose | — | — | — | 9.7 | — |
| | | Mannitol | — | — | — | — | 5.1 |
| | Pure water | | 90 | 90 | 90 | 90 | 90 |
| Physical property value | | Electrical conductivity (mS/m) | 0.5 | 0.5 | 0.6 | 0.6 | 0.6 |
| | | Osmotic pressure ratio to physiological saline | 1 | 1 | 1 | 1 | 1 |
| Evaluation | | Evaluation of ease of resection | B | B | B | B | A |
| | | Evaluation of safety (mass change rate) | 99% | 103% | 100% | 103% | 103% |
| | | Evaluation of elevation | A | A | A | A | A |

TABLE 4

| | | | Comparative Example 1 | Comparative Example 2 | Comparative Example 3 | Comparative Example 4 | Comparative Example 5 |
|---|---|---|---|---|---|---|---|
| Composition (parts by mass) | Specific water-soluble resin | Sodium hyaluronate A | — | — | 0.4 | — | 0.2 |
| | Specific organic compound | Glycerol | — | — | — | 4.2 | 10 |
| | Others | Polyethylene glycol 600 | — | — | — | — | — |
| | | Sodium chloride | 0.9 | 0.5 | — | — | 0.45 |
| | | Sodium dihydrogen phosphate | — | — | — | — | — |
| | | Disodium hydrogen phosphate | — | — | — | — | — |
| | | Sodium hyaluronate B | — | — | — | — | — |
| | Pure water | | 99 | 99 | 95 | 95 | 95 |
| Physical property value | | Electrical conductivity (mS/m) | 1520 | 810 | 95 | 0.5 | 820 |
| | | Osmotic pressure ratio to physiological saline | 1 | 0.55 | 0.1 | 1.6 | 4.3 |
| Evaluation | | Evaluation of ease of resection | E | D | A | A | D |
| | | Evaluation of safety (mass change rate) | 100% | 125% | 128% | 83% | 82% |
| | | Evaluation of elevation | E | E | C | C | D |

| | | | Comparative Example 6 | Comparative Example 7 | Comparative Example 8 | Comparative Example 9 |
|---|---|---|---|---|---|---|
| Composition (parts by mass) | Specific water-soluble resin | Sodium hyaluronate A | 0.2 | 0.4 | — | — |
| | Specific organic compound | Glycerol | — | — | 2.6 | 2.6 |
| | Others | Polyethylene glycol 600 | 17 | — | — | — |
| | | Sodium chloride | — | 0.8 | — | — |
| | | Sodium dihydrogen phosphate | — | 0.035 | — | — |
| | | Disodium hydrogen phosphate | — | 0.103 | — | — |
| | | Sodium hyaluronate B | — | — | — | 0.4 |
| | Pure water | | 80 | 95 | 95 | 95 |
| Physical property value | | Electrical conductivity (mS/m) | 50 | 1550 | 0.5 | 95 |
| | | Osmotic pressure ratio to physiological saline | 1 | 1 | 1 | 1 |
| Evaluation | | Evaluation of ease of resection | D | E | A | A |
| | | Evaluation of safety (mass change rate) | 98% | 102% | 104% | 102% |
| | | Evaluation of elevation | D | C | E | E |

From Table 1 to Table 4, it was found that the endoscopic submucosal injection materials prepared in the examples are excellent in ease of resection, safety, and elevation as compared to the endoscopic submucosal injection materials prepared in the comparative examples.

In addition, the specific organic compounds used in Examples 33 to 36 had a higher molecular weight than that of the specific organic compounds used in the other examples, and thus, the addition amount of the specific organic compounds used in Examples 33 to 36 to the endoscopic submucosal injection material for adjusting the osmotic pressure was large. Because the addition amount of the specific organic compound was increased, a level difference was generated in the elevated portion, which caused a deterioration in the ease of resection as compared to Example 1 and the like.

The entire content of the disclosure of Japanese Patent Application No. 2021-100418 filed Jun. 16, 2021 is incorporated in the present specification by reference. All documents, patent applications, and technical standards described in the present specification are incorporated in the present specification by reference such that each of the documents, the patent applications, and the technical standards is incorporated by reference to the same extent as the case in which each thereof is specifically and individually described.

What is claimed is:

1. An endoscopic submucosal injection material comprising:

a water-soluble resin having a weight-average molecular weight of 10,000 or more;

an organic compound having two or more hydroxyl groups and having a molecular weight of 400 or less; and water, wherein the endoscopic submucosal injection material has an electrical conductivity of 500 mS/m or less, an osmotic pressure ratio of the endoscopic submucosal injection material to physiological saline is 0.7 to 1.5, and the water-soluble resin comprises one or more compounds selected from the group consisting of sodium hyaluronate, sodium carboxymethyl cellulose, dextran, dextrin, sodium alginate, hydroxyalkyl cellulose, sodium carboxymethyl dextran, hydrophobized hydroxyalkyl cellulose, sodium poly(meth)acrylate, polyvinyl alcohol, gelatin, and casein.

2. The endoscopic submucosal injection material according to claim 1, wherein the organic compound comprises one or more compounds selected from the group including a glycol compound, a sugar alcohol compound, a monosaccharide compound, and a disaccharide compound.

3. The endoscopic submucosal injection material according to claim 1, wherein the organic compound comprises one or more glycol compounds selected from the group consisting of propylene glycol, triethylene glycol, and polyethylene glycol.

4. The endoscopic submucosal injection material according to claim 1, wherein the organic compound comprises one or more sugar alcohol compounds selected from the group consisting of erythritol, glycerol, sorbitol, and xylitol.

5. The endoscopic submucosal injection material according to claim 1, wherein a molecular weight of the organic compound is 200 or less.

6. The endoscopic submucosal injection material according to claim 1, wherein the organic compound comprises one or more compounds selected from the group consisting of erythritol, glycerol, sorbitol, glucose, propylene glycol, triethylene glycol, and polyethylene glycol.

7. The endoscopic submucosal injection material according to claim 1, wherein the molecular weight of the organic compound is 100 or less.

8. The endoscopic submucosal injection material according to claim 1, wherein a content of the organic compound with respect to the endoscopic submucosal injection material is 1.9% by mass to 9.0% by mass.

9. The endoscopic submucosal injection material according to claim 1, wherein a content of the water-soluble resin with respect to the endoscopic submucosal injection material is 0.1% by mass to 1.5% by mass.

* * * * *